(12) United States Patent
Santos

(10) Patent No.: US 7,044,923 B2
(45) Date of Patent: May 16, 2006

(54) APPARATUS AND METHOD FOR MEASURING A NERVE DIAMETER

(76) Inventor: Perry M. Santos, 5801 Wynstone Dr., Edmond, OK (US) 73034

( * ) Notice: Subject to any disclaimer, the term of this patent is extended or adjusted under 35 U.S.C. 154(b) by 0 days.

(21) Appl. No.: 10/980,403

(22) Filed: Nov. 2, 2004

(65) Prior Publication Data

US 2005/0101883 A1 May 12, 2005

Related U.S. Application Data

(60) Provisional application No. 60/519,508, filed on Nov. 12, 2003.

(51) Int. Cl.
*A61B 5/103* (2006.01)
*A61B 5/117* (2006.01)

(52) U.S. Cl. ..................................................... 600/587

(58) Field of Classification Search ................ 600/587, 600/594, 547, 202, 129; 33/511, 512, 514.1, 33/514.2, 501.15, 201, 202; 606/102
See application file for complete search history.

(56) References Cited

U.S. PATENT DOCUMENTS

| | | | | |
|---|---|---|---|---|
| 3,871,379 A | * | 3/1975 | Clarke | 606/148 |
| 4,503,568 A | * | 3/1985 | Madras | 623/1.3 |
| 5,486,183 A | * | 1/1996 | Middleman et al. | 606/127 |
| 5,755,750 A | * | 5/1998 | Petruska et al. | 607/75 |
| 6,600,956 B1 | * | 7/2003 | Maschino et al. | 607/118 |
| 2004/0199187 A1 | * | 10/2004 | Loughran | 606/152 |

\* cited by examiner

*Primary Examiner*—Max F. Hindenburg
*Assistant Examiner*—Rene Towa
(74) *Attorney, Agent, or Firm*—Jack C. Munro

(57) ABSTRACT

The present invention is generally directed to a nerve measurement apparatus, and to a method for measuring a nerve diameter. In one embodiment, the apparatus comprises an elongated shaft having a first end and an opposing second end, the first end and the second end being suitably configured to determine a diameter of a nerve. The first end may be further comprised of a pair of opposed prongs aligned with a longitudinal axis of the shaft and spaced apart by a predetermined distance to receive the nerve therebetween. The second end may be further comprised of a flexible self-coiling member having an inner diameter that conforms to the nerve diameter when the member is in a relaxed state.

4 Claims, 2 Drawing Sheets

RELAXED POSITION

PULLED OPEN POSITION

APPARATUS AND METHOD FOR MEASURING A NERVE DIAMETER

CROSS-REFERENCE(S) TO RELATED APPLICATION

This application claims the benefit of Provisional Application No. 60/519,508, filed Nov. 12, 2003.

TECHNICAL FIELD

The present invention relates generally to the measuring devices, and in particular, to a device for measuring a nerve diameter.

BACKGROUND OF THE INVENTION

Methods for treating and controlling medical, psychiatric or neurological disorders through the application of a modulated electrical signal to a selected nerve or nerve bundle in a patient are well known. Generally, the modulated signal is applied to the nerve or nerve bundle using a neurostimulator electrode assembly that is surgically implanted in the patient. Briefly, and in general terms, the neurostimulator electrode assembly comprises one or more electrodes positioned within a resilient circumneural carrier that is configured to be circumferentially positioned on the nerve. In order for the electrode to establish the requisite electrical contact with the nerve, the carrier must be able to securely hold the electrode against the nerve while not excessively circumferentially compressing the nerve. One example of a neurostimulator electrode assembly is shown and described in U.S. Pat. No. 6,600,956 B2 to Maschino, et al.

In order to accommodate nerves or nerve bundles of various diameters, neurostimulator electrode assemblies are available in standardized sizes that permit a surgeon to select the most appropriate size for implantation in a patient. Currently, the selection of the neurostimulator electrode assembly is made based upon a visual inspection of the nerve diameter. Selection of the electrode assembly by visual inspection has numerous drawbacks, however. If the surgeon selects an electrode assembly that has a diameter that is slightly too large, the electrodes within the assembly may fail to maintain adequate electrical contact with the nerve, as previously mentioned. If an electrode is selected that has a diameter that is too small, a nerve compression injury may result.

In order to overcome the shortcomings present in the visual estimation of a nerve diameter, the nerve diameter may be measured using conventional calipers of suitable size and resolution. Despite this obvious improvement, drawbacks nevertheless still exist. For example, a suitable measurement caliper may not be available to the surgeon while the implantation procedure is occurring. Even if a suitable caliper is available, conventional caliper devices generally possess relatively narrow tips that may cause the relatively compliant nerve to flatten during the measurement, thus rendering an inaccurate nerve diameter measurement.

Therefore, there is a need in the art for an accurate and inexpensive device to accurately measure a nerve diameter in order to achieve a consistent surgical outcome.

SUMMARY OF THE INVENTION

The present invention is generally directed to a nerve diameter measurement apparatus, and to a method for measuring a nerve diameter. In one aspect, the apparatus comprises an elongated shaft having a first end and an opposing second end, the first end and the second end being suitably configured to determine a diameter of a nerve. The first end may be further comprised of a pair of opposed prongs aligned with a longitudinal axis of the shaft and spaced apart by a predetermined distance to receive the nerve therebetween. The second end may be further comprised of a flexible self-coiling member having an inner diameter that conforms to the nerve diameter when the member is in a relaxed state.

DETAILED DESCRIPTION OF THE INVENTION

The present invention is generally directed to an apparatus and method for measuring a nerve diameter. Many of the specific details of certain embodiments of the invention are set forth in the following description and in FIGS. 1 to 7 to provide a thorough understanding of such embodiments. One skilled in the art will understand, however, that the present invention may be practiced without several of the details described in the following description. Moreover, in the description that follows, it is understood that the figures related to the various embodiments are not to be interpreted as conveying any specific or relative physical dimension. Instead, it is understood that specific or relative dimensions related to the embodiments, if stated, are not to be considered limiting unless the claims expressly state otherwise.

Figure 1:
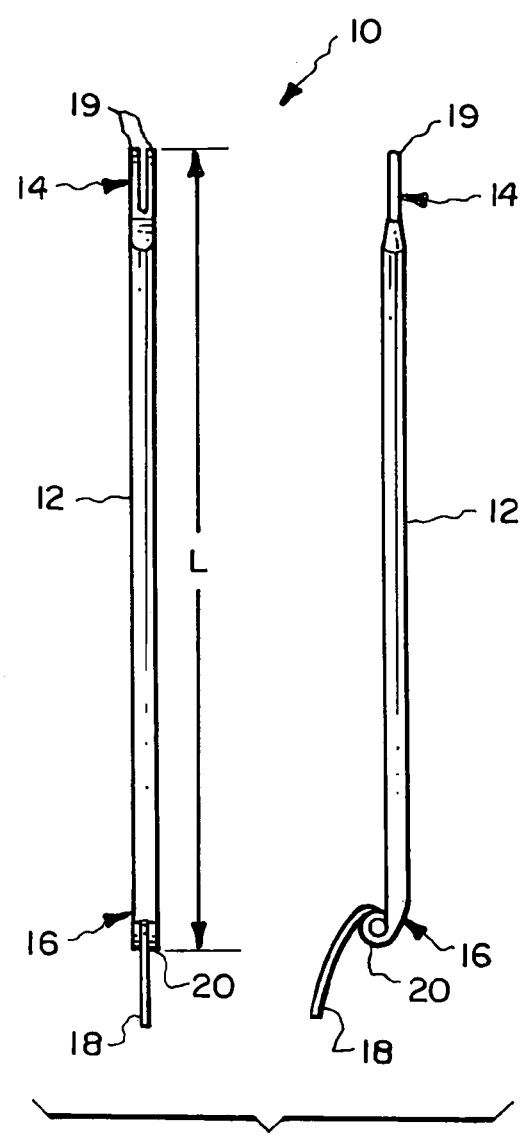
FIG. 1 is a front view and a side view of a nerve measurement apparatus according to an embodiment of the invention.

FIG. 1 is a front view and a side view of a nerve measurement apparatus 10 according to an embodiment of the invention. The apparatus 10 includes an elongated shaft 12 having a first end 14 and a second opposing end 16. The shaft 12 may be formed to have any suitable length L, but in one particular embodiment, the shaft 12 has a length L of approximately about 10 centimeters. Although FIG. 1 depicts the shaft 12 as a substantially straight, elongated member, it is understood that the shaft 12 may include bends or possess an overall curvature in order to allow the apparatus 10 to be more easily manipulated by the surgeon. The shaft 12 may be fabricated from any semi-rigid polymeric material suitable for use in surgical procedures and compatible with conventional sterilization procedures. In addition, the polymeric material comprising the shaft 12 may include a radio-opacifier, such as compounds of barium, or other materials, so that, in the event the apparatus 10 inadvertently remains in a patient's body following an implantation procedure, the shaft 12 may be conveniently imaged using an X-ray procedure. The shaft 12 may also include various color pigments so that the shaft 12 is easily visible. In another particular embodiment, one or more colors may be selected to correspond to a selected nerve diameter, as will be described in greater detail below.

Still referring to FIG. 1, the first end 14 includes a pair of spaced apart prongs that are substantially aligned with a longitudinal axis of the apparatus 10. The first end 14 will be described in greater detail below in connection with another figure. The second end 16 includes a flexible and self-coiling member 20 having a pull tab 18 fixedly attached to the member 20. The second end 16 will also be described in greater detail below in connection with another figure.

Figure 2:
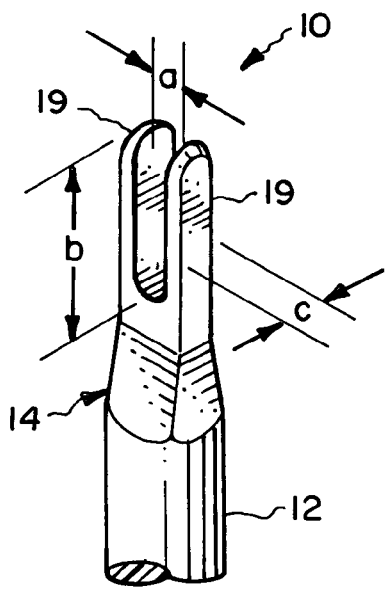
FIG. 2 is an enlarged partial isometric view of one end of a nerve measurement apparatus according to an embodiment of the invention.
Figure 3:
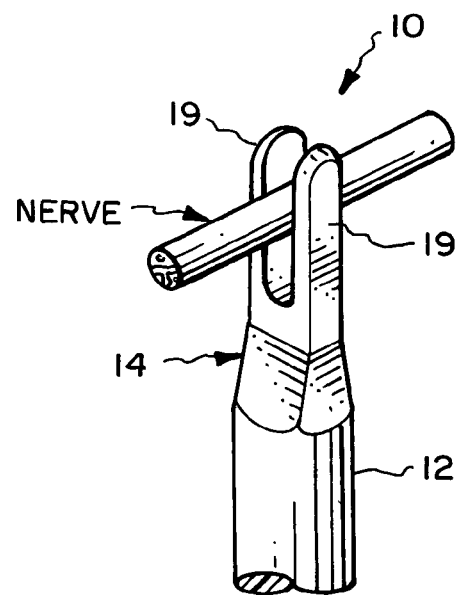
FIG. 3 is another partial isometric view of one end of a nerve measurement apparatus according to an embodiment of the invention.

FIG. 2 is an enlarged partial isometric view of the a nerve measurement apparatus 10 according to an embodiment of the invention that shows, in particular, the first end 14 of the apparatus 10. As described briefly above, the first end 14 includes a pair of spaced-apart prongs 19 that are substantially aligned with the longitudinal axis of the apparatus 10. In one particular embodiment, the first end 14 has a dimension "a" that is approximately about 2 millimeters, a dimension "b" that is approximately about 8 millimeters, and a dimension "c" that is approximately about 2 millimeters. Referring now to FIG. 3, the prongs 19 are suitably spaced apart and suitably dimensioned to accommodate a nerve between the prongs 19 and to permit a diameter of the nerve to be accurately and rapidly determined.

Figure 4:
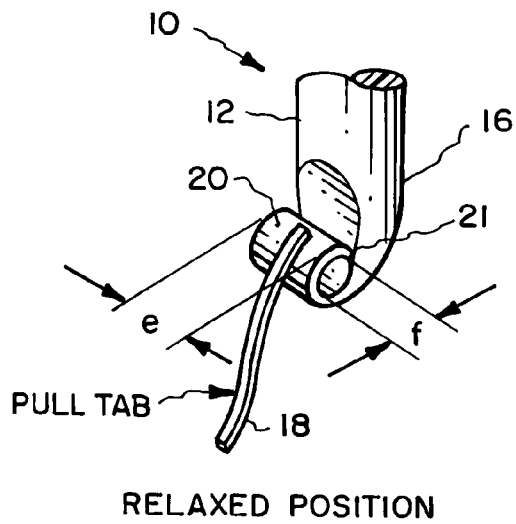
FIG. 4 is a partial isometric view of an opposing end of a nerve measurement apparatus according to an embodiment of the invention.
Figure 5:
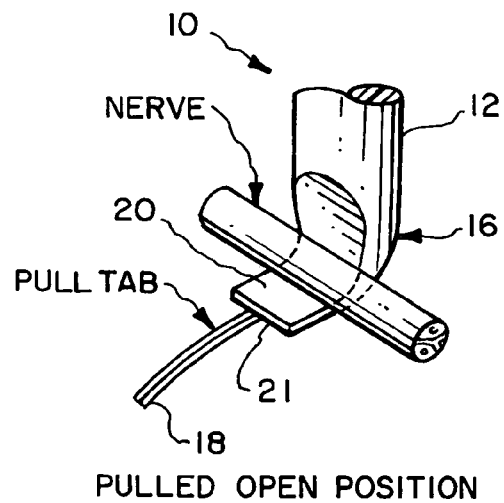
FIG. 5 is another partial isometric view of an opposing end of a nerve measurement apparatus according to an embodiment of the invention.

Turning now to FIGS. 4 and 5, a partial isometric view of the second end 16 of the nerve measurement apparatus 10 according to an embodiment of the invention is shown. The second end 16 includes a self-coiling member 20 that is positioned in a fully-coiled configuration, as shown in FIG. 4, when in a fully relaxed state, and also may be uncoiled by applying a pulling force to the pull tab 18, as shown in FIG. 5. In a particular embodiment, the self-coiling member 20 may have a width "e" of approximately about 3 millimeters, and an inner diameter "f" of approximately about 2 millimeters when the member 20 is in the relaxed state. When the self-coiling member 20 is in the uncoiled state, a nerve may be positioned adjacent to an interior portion of the member 20. The pulling force on the pull tab 18 may then be relaxed, allowing the member 20 to return to a coiled state and circumferentially surround the nerve. Accordingly, a diameter of a nerve may be made based upon the observed closure of the member 20 about the nerve, as will be discussed in greater detail below. The member 20 may be comprised of any resilient polymeric material capable of sufficient flexure, such as various silicone materials. In one particular embodiment, the member 20 may be formed from SILASTIC, available from the Dow Corning Corp. of Midland, Mich.

Figure 6:
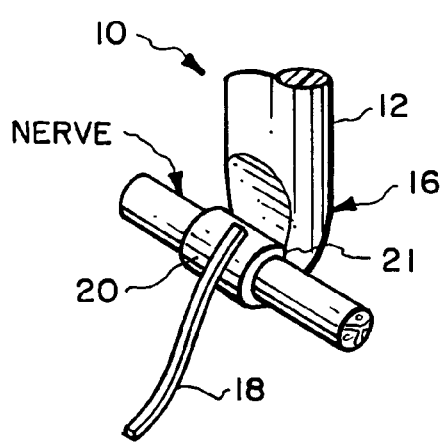
FIG. 6 is still another partial isometric view of an opposing end of a nerve measurement apparatus according to an embodiment of the invention.
Figure 7:
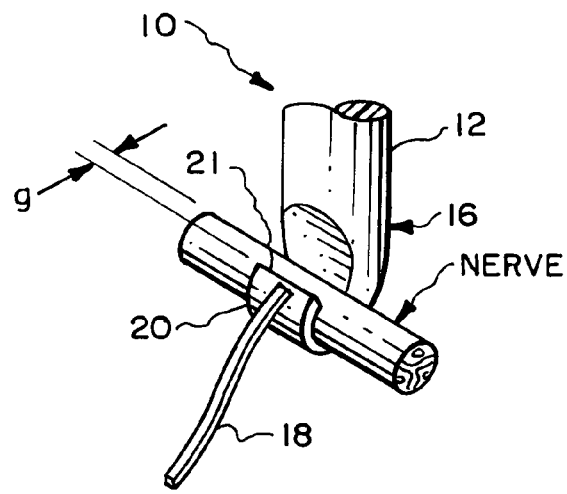
FIG. 7 is still another partial isometric view of an opposing end of a nerve measurement apparatus according to an embodiment of the invention.

Referring now to FIGS. 6 and 7, another partial isometric view of the second end 16 of the nerve measurement apparatus 10 according to an embodiment of the invention is shown. Many of the specific details of the second end 16 have been described in detail above, and in the interests of brevity, will not be described further. Instead, a method for measuring a nerve diameter using the second end 16 will now be described. Referring specifically to FIG. 6, when a nerve is retained within the fully coiled member 20 and an end portion 21 of the member 20 abuts the shaft 12, the diameter of the nerve corresponds to the known inner diameter of the member 20. Thus, the nerve diameter is easily and quickly determined. Referring specifically now to FIG. 7, when a nerve is retained within the fully coiled member 20 and an end portion 21 of the member 20 is spaced apart from the shaft 12 by a distance "g", it is determined by inspection that the diameter of the nerve is greater than the known inner diameter of the member 20. Accordingly, another apparatus 10 having a member 20 with a larger inner diameter "f" (see FIG. 4) may be selected in order to determine the actual diameter of the nerve.

From the foregoing it will be appreciated that, although specific embodiments of the invention have been described herein for purposes of illustration, various modifications may be made without deviating from the spirit and scope of the invention. For example, certain features shown in the context of one embodiment of the invention may be incorporated into other embodiments as well. Accordingly, the invention is not limited by the foregoing description of embodiments except as by the following claims.

The invention claimed is:

1. A method of measuring a diameter of a nerve comprising the steps of:
   utilizing a flexible self-coiling member that is locatable in a coiled configuration when at rest or in an uncoiled configuration when not at rest;
   locating and maintaining said member in said uncoiled configuration;
   placing a portion of a nerve against said member;
   allowing said member to return to said coiled configuration enclosing said nerve; and
   determining the diameter of the nerve by visually observing position of the member on the nerve.

2. The method as defined in claim 1 wherein the determining step is achieved by noting to the extent that the flexible self-coiling member encloses the nerve, as to whether it is completely closed or something less than completely closed.

3. The method of measuring the diameter of a nerve as defined in claim 2 wherein the step of determining includes comparing of the position of the self-coiling member on the nerve relative to known positions for different nerve diameters.

4. The method as defined in claim 3 wherein the determining step includes a distance that an end portion of the flexible self-coiling member is offset from a reference position when the self-coiling member is positioned on the nerve.

\* \* \* \* \*